US00PP20058P2

(12) United States Plant Patent

Shiozaki

(10) Patent No.: US PP20,058 P2

(45) Date of Patent: Jun. 2, 2009

(54) *DICENTRA* PLANT NAMED 'REKKA'

(50) Latin Name: *Dicentra×hybrida*
Varietal Denomination: Rekka

(76) Inventor: Akira Shiozaki, 234 Otoe, Otoe-cho, Fukagawa City, Hokkaido 074-1273 (JP)

( * ) Notice: Subject to any disclaimer, the term of this patent is extended or adjusted under 35 U.S.C. 154(b) by 0 days.

(21) Appl. No.: 12/082,723

(22) Filed: Apr. 14, 2008

(51) Int. Cl.
*A01H 5/00* (2006.01)

(52) U.S. Cl. ..... Plt./426

(58) Field of Classification Search ..... Plt./426
See application file for complete search history.

*Primary Examiner*—June Hwu

(74) *Attorney, Agent, or Firm*—Audrey Charles

(57) ABSTRACT

A new and distinct cultivar of *Dicentra* plant named 'Rekka', characterized by its rose-colored flowers, blue-grey colored foliage, and moderately vigorous, mounded growth habit.

1 Drawing Sheet

Latin name of genus and species of plant claimed: *Dicentra×hybrida.*

Variety denomination: 'Rekka'.

BACKGROUND OF THE INVENTION

The present invention relates to a new and distinct cultivar of *Dicentra* plant botanically known as *Dicentra×hybrida* and hereinafter referred to by the cultivar name 'Rekka'.

The new cultivar originated in a controlled breeding program in Fukagawa, Japan during July 2002. The objective of the breeding program was the development of *Dicentra* cultivars that are have fragrant flowers with unique flower coloration.

The new *Dicentra* cultivar is the result of cross-pollination. The female (seed) parent of the new cultivar is *Dicentra peregrine* 'Hien', not patented, characterized by its dark red-colored flowers, blue-grey colored foliage, and a mounded growth habit. The male (pollen) parent of the new cultivar is *Dicentra eximia,* not patented, characterized by its rose-colored flowers, blue grey-colored foliage, and vigorous, mounded growth habit. The new cultivar was discovered and selected as a single flowering plant within the progeny of the above stated cross-pollination during October 2004 in a controlled environment at Fukagawa, Japan.

Asexual reproduction of the new cultivar by terminal stem cuttings since October 2004 at Fukagawa, Japan has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Rekka' as a new and distinct cultivar of *Dicentra* plant:

1. Rose-colored flowers;
2. Blue-grey colored foliage; and
3. Moderately vigorous, mounded growth habit.

Plants of the new cultivar differ from plants of the female parent primarily in flower color and from plants of the male parent primarily in vigorousness of growth.

Of the many commercially available *Dicentra* cultivars, the most similar in comparison to the new cultivar is *Dicentra* 'King of Hearts', unpatented. However, in side by side comparisons, plants of the new cultivar differ from plants of 'King of Hearts' in the following characteristics:

1. Plants of the new cultivar have a darker red flower color than plants of 'King of Hearts'; and
2. Plants of the new cultivar have more silver colored foliage than plants of 'King of Hearts'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Rekka'. The plants were grown in 4.5 inch pots for 11 weeks in a greenhouse at West Chicago, Ill.

DETAILED BOTANICAL DESCRIPTION

Figure 1:
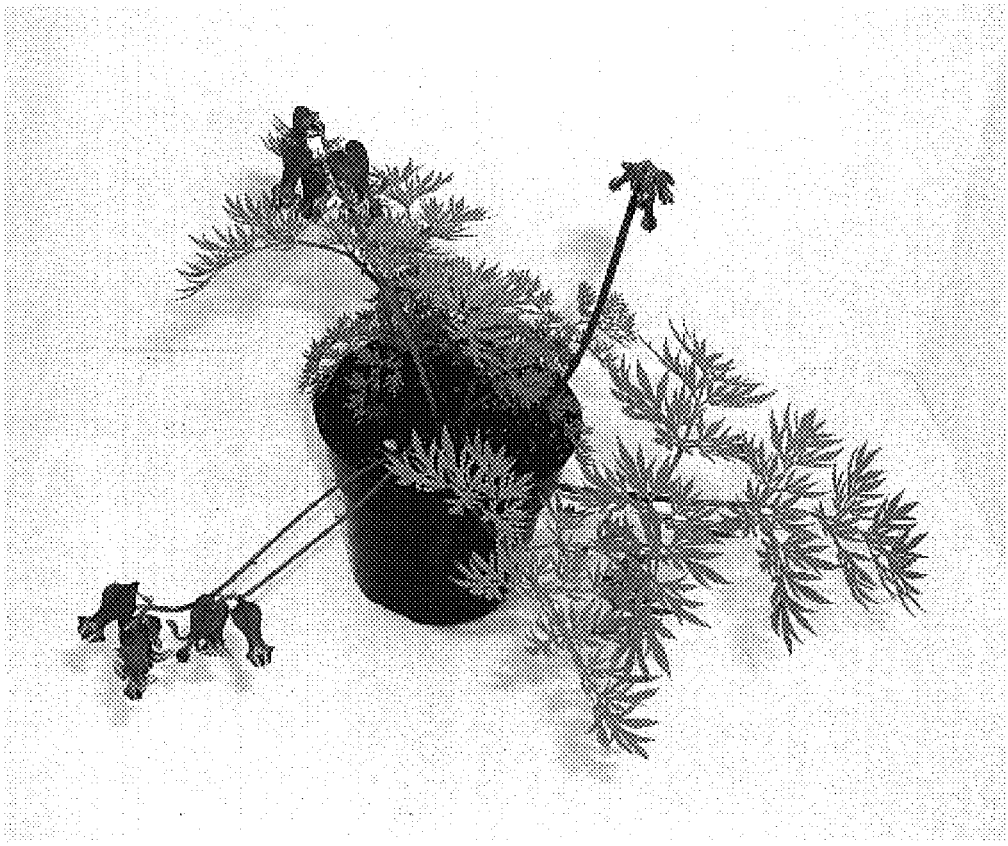
FIG. 1 illustrates a side view of the overall growth and flowering habit of 'Rekka'.
Figure 2:
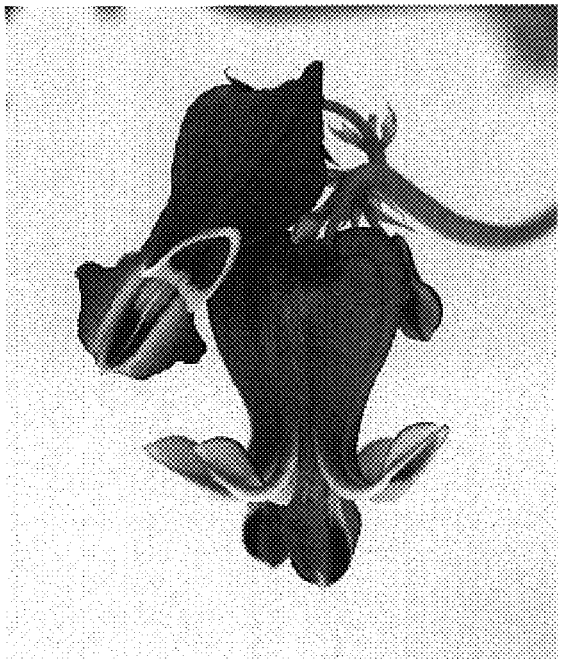
FIG. 2 illustrates a close-up view of an individual inflorescence of 'Rekka'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 17, 2007 between 1:00 p.m. and 3:00 p.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 11 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Dicentra×hybrida* cultivar Rekka.

Parentage:

*Female parent.*—*Dicentra peregrine* 'Hien', not patented.

*Male parent.*—*Dicentra eximia,* not patented.

Propagation:

*Type cutting.*—Root.

*Time to initiate roots.*—Approximately 7 to 14 days.

*Root description.*—Fine, rhizomatous.

*Rooting habit.*—Freely branching.

Plant description:

*Commercial crop time.*—Approximately 12 to 16 weeks from bareroot plant to finish in a one gallon plant.

*Growth habit and general appearance.*—Moderately vigorous, upright.

*Size.*—Height from soil level to top of plant plane: Approximately 21.0 cm. Width: Approximately 33.6 cm.

*Branching habit.*—Non-branching.

Foliage description:

*General description.*—Quantity of leaves per plant: Approximately 9. Fragrance: Strong. Form: Simple. Arrangement: Arise basally from central crown, and occasional cauline leaves on peduncle.

*Leaves.*—Shape: Broadly ovate. Margin: Deeply bipinnatifid. Apex of divisions: Acute. Base of divisions: Attenuate. Venation pattern: Pinnate. Length of basal leaf: Approximately 13.0 cm. Width of basal leaf: Approximately 13.2 cm. Texture of upper and lower surfaces: Glabrous. Color of upper surface of young foliage: 146A with indistinguishable venation. Color of lower surface of young foliage: 146B with an overlay of 187C with indistinguishable venation. Color of upper surface of mature foliage: Glaucous, N138A with indistinguishable venation. Color of lower surface of mature foliage: Slightly glaucous, closest to N138C with indistinguishable venation.

*Petiole.*—Length: Approximately 9.8 cm. Diameter: Approximately 2.3 mm. Texture: Glabrous. Color: 144A with an overlay of 187C.

Flowering description:

*Flowering habit.*—'Rekka' is typically freely flowering under outdoor growing conditions from early April until September.

*Lastingness of individual flower on the plant.*—Approximately 14 days.

Inflorescence description:

*General description.*—Type: Panicle. Quantity panicles per plant: Approximately 3. Fragrance: Slight perfume scent. Length or height: Approximately: 2.9 cm. Width: Approximately 5.1 cm. Quantity of fully open flowers per inflorescence: Approximately 4.

*Peduncle.*—Strength: Strong. Length or height: Approximately 17.4 cm. Width: Approximately 2.5 mm. Texture: Glabrous. Color: 144A with an overlay of 187C, overlay becomes less intense as peduncle matures.

*Rachis.*—Strength: Strong. Length or height: Approximately 4.5 cm. Width: Approximately 2.0 mm. Texture: Glabrous. Color: 144A with an overlay of 187C, overlay becomes less intense as peduncle matures.

Flower description:

*General description.*—Type: Single.

*Bud.*—Rate of opening: Generally takes 5 to 10 days for bud to progress from first color to fully open flower.

*Bud just before opening.*—Shape: Pitcher. Length: Approximately 2.5 cm. Diameter: Approximately 1.3 cm. Color: 60A.

*Corolla.*—Shape: Isobilateral, open heart. Aspect: Pendant, nodding. Length: Approximately 2.5 cm. Width: Approximately 2.1 cm.

*Petals.*—Quantity: 4 with one outer pair and one inner pair, fused at base.

*Outer petals.*—Shape: Cordate, folded longitudinally. Margin: Entire. Apex: Acute with a hooded appearance. Length: Approximately 1.9 cm. Width: Approximately 1.3 cm. Texture of outer and inner surfaces: Glabrous. Color of outer surface when fully open: 60B. Color of inner surface when fully open: 69D with a central spot of 71A at apex.

*Inner petals.*—Shape: Oblong, folded longitudinally. Margin: Entire. Apex: Rounded with a hooded appearance. Length: Approximately 2.5 cm. Width: Approximately 5.0 mm. Texture of outer and inner surfaces: Glabrous. Color of outer surface when fully open: 69D with streaks of 60B and a central spot of 71A at apex. Color of inner surface when fully open: 69D with spots of 71B and a central spot of 71A at apex.

*Calyx.*—Shape: Vestigial.

*Sepals.*—Quantity per flower: 2. Shape: Ovate. Apex: Acute. Base: Fused. Length: Approximately 3.0 mm. Width: Approximately 2.0 mm. Texture of outer and inner surfaces: Glabrous. Color of outer surface: 61A. Color of inner surface: 61B.

*Pedicel.*—Strength: Strong, flexible. Aspect: Obtuse angle to rachis. Length: Approximately 1.1 cm. Diameter: Approximately 1.0 mm. Texture: Glabrous. Color: 144A.

*Reproductive organs.*—Androecium: Stamen quantity: 2 per flower, each with a group of 3 anthers. Stamen length: Approximately 1.8 cm. Filament length: Approximately 1.7 cm. Filament color: N155B with streaks of 60B. Anther shape: Oval. Anther length: Approximately 1.0 mm. Anther color: 21A. Pollen amount: Abundant. Pollen color: 4D. Gynoecium: Pistil quantity: 1 per flower. Pistil length: Approximately 2.0 cm. Stigma shape: Crested, in 4 parts. Stigma length: Approximately 1.0 mm. Stigma color: N144A. Style length: Approximately 1.3 cm. Style color: N144C with an overlay of 187C. Ovary length: Approximately 5.7 mm. Ovary color: N144C with an overlay of 187C.

Seed and fruit production: Neither seed nor fruit production was observed.

Disease and pest resistance: Resistance to pathogens and pests common to *Dicentra* was not observed.

What is claimed is:

1. A new and distinct cultivar of *Dicentra* plant named 'Rekka', substantially as herein shown and described.

* * * * *